(12) United States Patent
Gross et al.

(10) Patent No.: US 9,265,945 B2
(45) Date of Patent: *Feb. 23, 2016

(54) RETINAL PROSTHESIS

(75) Inventors: Yossi Gross, Moshav Mazor (IL); Shai Vaingast, Ganei Tikva (IL); Ra'anan Gefen, Reut (IL)

(73) Assignee: NANO-RETINA, INC., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 13/148,461

(22) PCT Filed: Feb. 3, 2010

(86) PCT No.: PCT/IL2010/000097
§ 371 (c)(1),
(2), (4) Date: Nov. 4, 2011

(87) PCT Pub. No.: WO2011/163262
PCT Pub. Date: Dec. 29, 2011

(65) Prior Publication Data
US 2012/0041514 A1 Feb. 16, 2012

Related U.S. Application Data

(63) Continuation-in-part of application No. 12/368,150, filed on Feb. 9, 2009, now Pat. No. 8,150,526.

(51) Int. Cl.
*A61N 1/36* (2006.01)
*A61N 1/372* (2006.01)
(Continued)

(52) U.S. Cl.
CPC .......... *A61N 1/36046* (2013.01); *A61N 1/3787* (2013.01); *A61N 1/37217* (2013.01); *H01L 27/14621* (2013.01); *H01L 27/14627* (2013.01); *H01L 31/145* (2013.01); *A61N 1/0543* (2013.01)

(58) Field of Classification Search
CPC ............ A61N 1/36046; A61N 1/0543; A61N 1/3787; A61N 1/36146; A61N 1/37217; A61B 5/6821; H04N 5/2254; A61F 2/14; H01L 27/14621; H01L 27/14627

USPC .......................................................... 607/53
See application file for complete search history.

(56) References Cited

U.S. PATENT DOCUMENTS 1,662,446 A    3/1928  Wappler
2,721,316 A   10/1955  Shaw
(Continued)

FOREIGN PATENT DOCUMENTS

CA    2235216 A1    4/1997
CA    2235316       4/1997
(Continued)

OTHER PUBLICATIONS

Delbruck and Mead, "Analog VLSI Adptive, Logarithmic, Wide-dynamic-Range Photoreceptor," 1994 International Symposium on Circuits and Systems (London, 1994), pp. 339-342.
(Continued)

*Primary Examiner* — Michael Kahelin
*Assistant Examiner* — Minh Duc Pham
(74) *Attorney, Agent, or Firm* — Sughrue Mion, PLLC

(57) ABSTRACT

An external device (20) includes a mount (22), which is placed in front of a subject's eye. A laser (24) is coupled to the mount (22) and emits radiation (26) that is outside of 380-750 nm. A partially-transparent mirror (23) is coupled to the mount (22). An intraocular device (30) is implanted entirely in the subject's eye, and includes a plurality of stimulating electrodes (38), and an energy receiver (32), which receives the radiation (26) from the laser (24) and generates a voltage drop. A plurality of photosensors (34) detect photons (33) and generate a signal. Driving circuitry (36) is coupled to the energy receiver (32) and to the photosensors (34), and receives the signals from the photosensors (34) and utilizes the voltage drop to drive the electrodes (38) to apply currents to the retina in response to the signals from the photosensors (34). Other embodiments are also described.

21 Claims, 4 Drawing Sheets

(51) Int. Cl.
  *A61N 1/378* (2006.01)
  *H01L 27/146* (2006.01)
  *H01L 31/14* (2006.01)
  *A61N 1/05* (2006.01)

(56) References Cited

U.S. PATENT DOCUMENTS

| | | | |
|---|---|---|---|
| 2,760,483 A | 8/1956 | Graham |
| 4,262,294 A | 4/1981 | Hara et al. |
| 4,272,910 A | 6/1981 | Danz |
| 4,551,149 A | 11/1985 | Sciarra |
| 4,601,545 A | 7/1986 | Kern |
| 4,628,933 A | 12/1986 | Michelson |
| 4,664,117 A | 5/1987 | Beck |
| 4,786,818 A | 11/1988 | Mead et al. |
| 4,837,049 A | 6/1989 | Byers et al. |
| 4,903,702 A | 2/1990 | Putz |
| 4,914,738 A | 4/1990 | Oda et al. |
| 4,969,468 A | 11/1990 | Byers et al. |
| 5,016,633 A | 5/1991 | Chow |
| 5,024,223 A | 6/1991 | Chow |
| 5,081,378 A | 1/1992 | Watanabe |
| 5,108,427 A | 4/1992 | Majercik et al. |
| 5,109,844 A | 5/1992 | de Juan, Jr. et al. |
| 5,133,356 A | 7/1992 | Bryan et al. |
| 5,147,284 A | 9/1992 | Fedorov et al. |
| 5,159,927 A | 11/1992 | Schmid |
| 5,215,088 A | 6/1993 | Normann et al. |
| 5,313,642 A | 5/1994 | Seigel |
| 5,314,458 A | 5/1994 | Najafi et al. |
| 5,397,350 A | 3/1995 | Chow et al. |
| 5,411,540 A | 5/1995 | Edell et al. |
| 5,476,494 A | 12/1995 | Edell et al. |
| 5,526,423 A | 6/1996 | Ohuchi et al. |
| 5,556,423 A | 9/1996 | Chow et al. |
| 5,575,813 A | 11/1996 | Edell et al. |
| 5,597,381 A | 1/1997 | Rizzo, III |
| 5,608,204 A | 3/1997 | Hofflinger et al. |
| 5,674,263 A | 10/1997 | Yamamoto et al. |
| 5,769,875 A | 6/1998 | Peckham et al. |
| 5,800,478 A | 9/1998 | Chen et al. |
| 5,800,533 A | 9/1998 | Eggleston et al. |
| 5,800,535 A | 9/1998 | Howard, III |
| 5,835,250 A | 11/1998 | Kanesaka |
| 5,836,996 A | 11/1998 | Doorish |
| 5,837,995 A | 11/1998 | Chow et al. |
| 5,850,514 A | 12/1998 | Gonda et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 5,949,064 A | 9/1999 | Chow et al. |
| 6,020,593 A | 2/2000 | Chow et al. |
| 6,032,062 A | 2/2000 | Nisch |
| 6,035,236 A | 3/2000 | Jarding et al. |
| 6,043,437 A | 3/2000 | Schulman et al. |
| 6,069,365 A | 5/2000 | Chow et al. |
| 6,075,251 A | 6/2000 | Chow et al. |
| 6,201,234 B1 | 3/2001 | Chow et al. |
| 6,230,057 B1 | 5/2001 | Chow et al. |
| 6,259,937 B1 | 7/2001 | Schulman et al. |
| 6,287,372 B1 | 9/2001 | Briand et al. |
| 6,298,270 B1 | 10/2001 | Nisch et al. |
| 6,324,429 B1 | 11/2001 | Shire et al. |
| 6,347,250 B1 | 2/2002 | Nisch et al. |
| 6,368,349 B1 | 4/2002 | Wyatt et al. |
| 6,389,317 B1 | 5/2002 | Chow et al. |
| 6,400,989 B1 * | 6/2002 | Eckmiller ........ A61N 1/36046 607/54 |
| 6,427,087 B1 | 7/2002 | Chow et al. |
| 6,442,431 B1 | 8/2002 | Veraart et al. |
| 6,458,157 B1 | 10/2002 | Suaning |
| 6,472,122 B1 | 10/2002 | Schulman et al. |
| 6,498,043 B1 | 12/2002 | Schulman et al. |
| 6,507,758 B1 | 1/2003 | Greenberg et al. |
| 6,533,798 B2 | 3/2003 | Greenberg et al. |
| 6,574,022 B2 | 6/2003 | Chow et al. |
| 6,611,716 B2 | 8/2003 | Chow et al. |
| 6,647,297 B2 | 11/2003 | Scribner |
| 6,658,299 B1 | 12/2003 | Dobelle |
| 6,677,225 B1 | 1/2004 | Ellis et al. |
| 6,678,458 B2 | 1/2004 | Ellis et al. |
| 6,683,645 B1 | 1/2004 | Collins et al. |
| 6,738,672 B2 | 5/2004 | Schulman et al. |
| 6,755,530 B1 | 6/2004 | Loftus et al. |
| 6,758,823 B2 | 7/2004 | Pasquale et al. |
| 6,761,724 B1 | 7/2004 | Zrenner et al. |
| 6,762,116 B1 | 7/2004 | Skidmore |
| 6,770,521 B2 | 8/2004 | Visokay et al. |
| 6,785,303 B1 | 8/2004 | Holzwarth et al. |
| 6,792,314 B2 | 9/2004 | Byers et al. |
| 6,804,560 B2 | 10/2004 | Nisch et al. |
| 6,821,154 B1 | 11/2004 | Canfield et al. |
| 6,844,023 B2 | 1/2005 | Schulman et al. |
| 6,847,847 B2 | 1/2005 | Nisch et al. |
| 6,888,571 B1 * | 5/2005 | Koshizuka ........ H04N 5/353 348/222.1 |
| 6,904,239 B2 | 6/2005 | Chow et al. |
| 6,908,470 B2 | 6/2005 | Stieglitz et al. |
| 6,923,669 B1 | 8/2005 | Tsui et al. |
| 6,935,897 B2 | 8/2005 | Canfield et al. |
| 6,949,763 B2 | 9/2005 | Ovadia et al. |
| 6,961,619 B2 | 11/2005 | Casey |
| 6,970,745 B2 | 11/2005 | Scribner |
| 6,974,533 B2 | 12/2005 | Zhou |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 * | 2/2006 | Chow ............... A61F 9/08 607/54 |
| 7,025,619 B2 | 4/2006 | Tsui et al. |
| 7,027,874 B1 | 4/2006 | Sawan et al. |
| 7,031,776 B2 | 4/2006 | Chow et al. |
| 7,035,692 B1 | 4/2006 | Maghribi et al. |
| 7,037,943 B2 | 5/2006 | Peyman |
| 7,047,080 B2 | 5/2006 | Palanker et al. |
| 7,058,455 B2 | 6/2006 | Huie, Jr. et al. |
| 7,071,546 B2 | 7/2006 | Fey et al. |
| 7,079,881 B2 | 7/2006 | Schulman et al. |
| 7,081,630 B2 | 7/2006 | Saini et al. |
| 7,096,568 B1 | 8/2006 | Nilsen et al. |
| 7,103,416 B2 | 9/2006 | Ok et al. |
| 7,107,097 B2 | 9/2006 | Stern et al. |
| 7,127,286 B2 | 10/2006 | Mech et al. |
| 7,127,301 B1 | 10/2006 | Okandan et al. |
| 7,130,693 B1 | 10/2006 | Montalbo |
| 7,133,724 B2 | 11/2006 | Greenberg et al. |
| 7,139,612 B2 | 11/2006 | Chow et al. |
| 7,147,865 B2 | 12/2006 | Fishman et al. |
| 7,149,586 B2 | 12/2006 | Greenberg et al. |
| 7,158,834 B2 | 1/2007 | Paul, Jr. |
| 7,158,836 B2 | 1/2007 | Suzuki |
| 7,160,672 B2 | 1/2007 | Schulman et al. |
| 7,162,308 B2 | 1/2007 | O'Brien et al. |
| 7,177,697 B2 | 2/2007 | Eckmiller et al. |
| 7,190,051 B2 | 3/2007 | Mech et al. |
| 7,191,010 B2 | 3/2007 | Ohta et al. |
| 7,224,300 B2 | 5/2007 | Dai et al. |
| 7,224,301 B2 | 5/2007 | Dai et al. |
| 7,235,350 B2 | 6/2007 | Schulman et al. |
| 7,242,597 B2 | 7/2007 | Shodo |
| 7,244,027 B2 | 7/2007 | Sumiya |
| 7,248,928 B2 * | 7/2007 | Yagi ............... A61F 2/14 607/139 |
| 7,251,528 B2 | 7/2007 | Harold |
| 7,255,871 B2 | 8/2007 | Huie, Jr. et al. |
| 7,257,446 B2 | 8/2007 | Greenberg et al. |
| 7,263,403 B2 | 8/2007 | Greenberg et al. |
| 7,271,525 B2 | 9/2007 | Byers et al. |
| 7,272,447 B2 | 9/2007 | Stett et al. |
| 7,291,540 B2 | 11/2007 | Mech et al. |
| 7,295,872 B2 | 11/2007 | Kelly et al. |

(56) References Cited

U.S. PATENT DOCUMENTS

| | | |
|---|---|---|
| 7,302,598 B2 | 11/2007 | Suzuki et al. |
| 7,314,474 B1 | 1/2008 | Greenberg et al. |
| 7,321,796 B2 | 1/2008 | Fink et al. |
| 7,342,427 B1 | 3/2008 | Fensore et al. |
| 7,377,646 B2 | 5/2008 | Suzuki |
| 7,379,000 B2 | 5/2008 | Dai et al. |
| 7,388,288 B2 | 6/2008 | Solzbacher et al. |
| 7,400,021 B2 | 7/2008 | Wu et al. |
| 7,447,547 B2 | 11/2008 | Palanker |
| 7,447,548 B2 | 11/2008 | Eckmiller |
| 7,480,988 B2 | 1/2009 | Ok et al. |
| 7,481,912 B2 | 1/2009 | Stelzle et al. |
| 7,482,957 B2 | 1/2009 | Dai et al. |
| 7,483,751 B2 | 1/2009 | Greenberg et al. |
| 7,493,169 B2 | 2/2009 | Greenberg et al. |
| 7,499,754 B2 | 3/2009 | Greenberg et al. |
| 7,539,544 B2 | 5/2009 | Greenberg et al. |
| 7,555,328 B2 | 6/2009 | Schulman et al. |
| 7,556,621 B2 | 7/2009 | Palanker et al. |
| 7,565,202 B2 | 7/2009 | Greenberg et al. |
| 7,565,203 B2 | 7/2009 | Greenberg et al. |
| 7,571,004 B2 | 8/2009 | Roy et al. |
| 7,571,011 B2 | 8/2009 | Zhou et al. |
| 7,574,263 B2 | 8/2009 | Greenberg et al. |
| 7,610,098 B2 | 10/2009 | McLean |
| 7,622,702 B2 | 11/2009 | Wu et al. |
| 7,630,771 B2 | 12/2009 | Cauller |
| 7,631,424 B2 | 12/2009 | Greenberg et al. |
| 7,638,032 B2 | 12/2009 | Zhou et al. |
| 7,666,523 B2 | 2/2010 | Zhou |
| 7,676,274 B2 | 3/2010 | Hung et al. |
| 7,691,252 B2 | 4/2010 | Zhou et al. |
| 7,706,887 B2 | 4/2010 | Tai et al. |
| 7,706,893 B2 | 4/2010 | Hung et al. |
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 | 11/2010 | Humayun et al. |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,989,080 B2 | 8/2011 | Greenberg et al. |
| 8,000,804 B1* | 8/2011 | Wessendorf ......... A61N 1/0543 607/115 |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2 | 9/2011 | Schulman et al. |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2 | 4/2012 | Gross et al. |
| 8,150,534 B2 | 4/2012 | Greenberg et al. |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,200,338 B2 | 6/2012 | Grennberg et al. |
| 8,226,661 B2 | 7/2012 | Balling et al. |
| 8,239,034 B2 | 8/2012 | Greenberg et al. |
| 8,244,362 B2 | 8/2012 | Yonezawa |
| 8,428,740 B2 | 4/2013 | Gefen et al. |
| 2001/0011844 A1 | 8/2001 | Ernst et al. |
| 2002/0091421 A1 | 7/2002 | Greenberg et al. |
| 2003/0023297 A1 | 1/2003 | Byers et al. |
| 2003/0032946 A1 | 2/2003 | Fishman et al. |
| 2003/0132946 A1 | 7/2003 | Gold |
| 2003/0181957 A1 | 9/2003 | Greenberg |
| 2003/0208248 A1 | 11/2003 | Carter et al. |
| 2004/0054407 A1* | 3/2004 | Tashiro ............... H01L 27/146 623/6.22 |
| 2004/0078064 A1 | 4/2004 | Suzuki |
| 2004/0080026 A1 | 4/2004 | Minamio et al. |
| 2004/0082981 A1 | 4/2004 | Chow et al. |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0015120 A1* | 1/2005 | Seibel .................. A61F 9/08 607/54 |
| 2005/0119605 A1 | 6/2005 | Sohn |
| 2005/0146954 A1 | 7/2005 | Win et al. |
| 2005/0168569 A1 | 8/2005 | Igarashi |
| 2006/0106432 A1 | 5/2006 | Sawan et al. |
| 2006/0111757 A9 | 5/2006 | Greenberg et al. |
| 2006/0184245 A1 | 8/2006 | Graf et al. |
| 2006/0282128 A1 | 12/2006 | Tai et al. |
| 2006/0287688 A1 | 12/2006 | Yonezawa |
| 2007/0005116 A1 | 1/2007 | Lo |
| 2007/0123766 A1 | 5/2007 | Whalen et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1 | 9/2008 | Arle et al. |
| 2008/0262571 A1 | 10/2008 | Greenberg et al. |
| 2008/0288036 A1 | 11/2008 | Greenberg et al. |
| 2008/0288067 A1 | 11/2008 | Flood |
| 2008/0294224 A1 | 11/2008 | Greenberg |
| 2009/0002034 A1 | 1/2009 | Westendorp et al. |
| 2009/0005835 A1 | 1/2009 | Greenberg et al. |
| 2009/0024182 A1 | 1/2009 | Zhang et al. |
| 2009/0118805 A1 | 5/2009 | Greenberg et al. |
| 2009/0192571 A1 | 7/2009 | Stett et al. |
| 2009/0204207 A1 | 8/2009 | Blum et al. |
| 2009/0204212 A1 | 8/2009 | Greenberg et al. |
| 2009/0216295 A1 | 8/2009 | Zrenner et al. |
| 2009/0228069 A1 | 9/2009 | Dai et al. |
| 2009/0287275 A1 | 11/2009 | Suaning et al. |
| 2009/0326623 A1 | 12/2009 | Greenberg et al. |
| 2010/0087895 A1 | 4/2010 | Zhou et al. |
| 2010/0174224 A1 | 7/2010 | Sohn |
| 2010/0204754 A1 | 8/2010 | Gross |

(56) References Cited

U.S. PATENT DOCUMENTS

| | | |
|---|---|---|
| 2010/0249877 A1 | 9/2010 | Naughton |
| 2010/0249878 A1 | 9/2010 | McMahon et al. |
| 2010/0331682 A1 | 12/2010 | Stein et al. |
| 2011/0054583 A1 | 3/2011 | Litt et al. |
| 2011/0172736 A1 | 7/2011 | Gefen et al. |
| 2011/0254661 A1 | 10/2011 | Fawcett et al. |
| 2012/0035725 A1 | 2/2012 | Gefen et al. |
| 2012/0035726 A1 | 2/2012 | Gross |
| 2012/0041514 A1 | 2/2012 | Gross et al. |
| 2012/0194781 A1 | 8/2012 | Agurok |
| 2012/0209350 A1 | 8/2012 | Taylor et al. |
| 2012/0221103 A1 | 8/2012 | Liran et al. |
| 2012/0259410 A1 | 10/2012 | Gefen et al. |
| 2012/0268080 A1 | 10/2012 | Jeon et al. |
| 2013/0126713 A1 | 5/2013 | Haas et al. |
| 2013/0322462 A1 | 12/2013 | Poulsen |
| 2014/0047713 A1 | 2/2014 | Singh et al. |

FOREIGN PATENT DOCUMENTS

| | | |
|---|---|---|
| CN | 1875895 | 12/2006 |
| DE | 10315397 | 10/2004 |
| DE | 10315397 A1 | 10/2004 |
| JP | 2000-350742 | 12/2000 |
| WO | 01/74444 | 10/2001 |
| WO | WO-01/91854 A1 | 12/2001 |
| WO | WO-03/032946 A2 | 4/2003 |
| WO | WO-2007/009539 A2 | 1/2007 |
| WO | 2007/076347 | 7/2007 |
| WO | WO-2007/095395 A2 | 8/2007 |
| WO | WO-2010/035173 A1 | 4/2010 |
| WO | WO-2010/089739 A2 | 8/2010 |
| WO | WO-2011/086545 A2 | 7/2011 |
| WO | WO 2011/163262 A2 | 12/2011 |
| WO | WO-2012/017426 A1 | 2/2012 |
| WO | WO-2012/114327 A2 | 8/2012 |
| WO | WO-2012/153325 A2 | 11/2012 |

OTHER PUBLICATIONS

Grill W., et al., Annual. Review of Biomedical. Engineering vol. 11: 1-24, 2009—Abstract.

Jourdain R P., et al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.

Kim B., "Through-Silicon-Via Copper Deposition for Vertical Chip Integration" Master. Res. Soc. Symp. Proc. vol. 970, 2007 Material Research Society.

Lianga C, et al., "Surface modification of cp-Ti using femtosecond laser micromachining and the deposition of Ca/P layer" Materials Letters vol. 62, Issue 23, Aug. 31, 2008, pp. 3783-3786—Abstract.

Ng, David, C. et al., "Pulse frequency modulation based CMOS image sensor for subretinal stimulation" IEEE Transactions on Circuits and Systems-II: Express Briefs, vol. 53, No. 6, Jun. 2006.

Palanker D. et al., "Design of a high-resolution optoelectric retinal prosthesis". Journal of Neural Engineering, Institute of physics publishing, Bristol, GB. vol. 2, No. 1, Mar. 1, 2005, pp. S105-S120, XP002427333, ISSN: 1741-2552, DOI: 10.1088/1741-2560/2/1/012.

Pelayo et al.: "Cortical Visual Neuro-Prosthesis for the Blind: Retina-Like Software/Hardware Preprocessor", Dept. of Computer Architecture and Technology, University of Granada, Spain 2Dept. of Histology and Institute of Bioengineering, University Miguel Hernandez, Alicante, Spain Neural Engineering, 2003. Conference Proceedings. First International IEEE EMBS Conference.

Puech M., et al., "Fabrication of 3D packaging TSV using DRIE" ALCATEL Micro Machining Systems, www.adixen.com, Mar. 2007.

M. Schwarz et al.: "Single-Chip CMOS Image Sensors for a Retina Implant System", Markus Schwarz, Ralf Hauschild, Bedrich J. Hosticka, Senior Member, IEEE, Jurgen Huppertz, Student Member, IEEE, Thorsten Kneip, Member, IEEE, Stephan Kolnsberg, Lutz Ewe, and Hoc Khiem Trieu, 2000.

Seo J M., et al., "Biocompatibility of polyimide microelectrode array for retinal stimulation," Materials Science and Engineering: C, vol. 24, No. 1, Jan. 5, 2004, pp. 185-189(5).

Sorkin R., et al., "Process entanglement as a neuronal anchorage mechanism to rough surfaces," Nanotechnology 20 (2009) 015101 (8 pp).

Starzyk JA, et al., "A DC-DC charge pump design based on voltage doublers" IEEE Transaction on Circuits and Systems-I: Fundamental theory and applications, vol. 48, No. 3 Mar. 2001.

Stein DJ, et al., "High voltage with Si series photovoltaics" Proceedings of SPIE, the International Society for Optical Engineering 2006, vol. 6287, pp. 62870D.1-62870D.

Swain P K., et al., "Back-Illuminated Image Sensors Come to the Forefront. Novel materials and fabrication methods increase quality and lower cost of sensors for machine vision and industrial imaging." Photonics Spectra Aug. 2008.

Vorobyeva A Y. et al., "Metallic light absorbers produced by femtosecond laser pulses," Advances in Mechanical Engineering vol. 2010, Article ID 452749, 4 pages, doi:10.1155/2010/452749, Hindawi Publishing Corporation.

Vorobyeva A Y. et al., "Femtosecond laser structuring of titanium implants," Applied Surface Science vol. 253, Issue 17, Jun. 30, 2007, pp. 7272-7280—Abstract.

Wallman L., et al., "The geometric design of micromachined silicon sieve electrodes influences functional nerve regeneration," Biomaterials May 2001:22(10):1187-93—Abstract.

Warren M. Grill, et al. "Implanted Neural Interfaces: Biochallenges and Engineered Solutions", Annu. Rev. Biomed. Eng. 2009, 11:1-24.

Walter P., et al., "Cortical Activation via an implanted wireless retinal prosthesis," Investigative Ophthalmology and Visual Science. 2005;46:1780-1785.

Wu J T. and Chang K L., "MOS charge pumps for low-voltage operation" IEEE Journal of Solid-State Circuits, vol. 33 No. 4 Apr. 1998.

Zrenner E., 2002. "Will retinal implants restore vision" Science 295 (5557), pp. 1022-1025.

http://www.sony.net/SonyInfo/News/Press/200806/08-069E/index.html.

International Search Report and a Written Opinion both dated Dec. 12, 2011, which issued during the prosecution of Applicant's PCT/IL11/00609.

International Preliminary Report on Patentability and a Written Opinion both dated Aug. 9, 2011, which issued during the prosecution of Applicant's PCT/IL10/00097.

International Preliminary Report on Patentability dated Jul. 17, 2012, which issued during the prosecution of Applicants PCT/IL2011/000022.

International Search Report dated Aug. 12, 2011, which issued during the prosecution of Applicant's PCT/IL2011/000022.

International Search Report dated Aug. 17, 2010, which issued during the prosecution of Applicant's PCT/IL10/00097.

International Search Report and a Written Opinion both dated Sep. 17, 2012, which issued during the prosecution of Applicant's PCT/IL12/00057.

Office Action dated Aug. 24, 2011, which issued during the prosecution of U.S. Appl. No. 12/368,150.

Office Action dated Dec. 14, 2011, which issued during the prosecution of U.S. Appl. No. 12/368,150.

Office Action dated Aug. 28, 2012, which issued during the prosecution of U.S. Appl. No. 12/852,218.

Office Action dated Sep. 28, 2012, which issued during the prosecution of U.S. Appl. No. 13/103,264.

Supplementary European Search Report dated Aug. 10, 2012, which issued during the prosecution of Applicants European Application No. 10 73 8277.

Office Action for U.S. Appl. No. 12/687,509, dated Jun. 6, 2013.

European Search Report for European Application No. EP 11 73 2733, dated Jul. 16, 2013.

(56) References Cited

OTHER PUBLICATIONS

Tran et al., "A Fully Flexible Stimulator using 65 nm CMOS Process for 1024-electrode Epi-retinal Prosthesis," 31st Annual International Conference of the IEEE EMBS, Minneapolis, Minnesota, Sep. 2-6, 2009.

Normann et al., "High-resolution spatio-temporal mapping of visual pathways using multi-electrode arrays," Vision Research 41:1261-1275 (2001).

Yoo et al., "Excimer laser deinsulation of Parylene-C on iridium for use in an activated iridium oxide film-coated Utah electrode array," Journal of Neuroscience Methods, 215:78-87 (2013).

Office Action issued Dec. 7, 2012 in connection with U.S. Appl. No. 12/687,509.

Office Action issued Dec. 14, 2012 in connection with U.S. Appl. No. 13/034,516.

K. Ganesan et al.: "Diamond Penetrating Electrode Array for Epi-Retinal Prosthesis," 32nd Annual International Conference of the IEEE EMBS, Buenos Aires, Argentina, Aug. 31-Sep. 4, 2010, pp. 6757-6760.

W. E. Finn, et al.: "An Amphibian Model for Developing and Evaluating Retinal Prosthesis," 18the Annual International Conference of the IEEE EMBS, Amsterdam 1996, pp. 1540-1541.

M. Schwarz, et al.: "Hardware Architecture of a Neural Net Based Retina Implant for Patients Suffering from Retinitis Pigmentosa," Fraunhofer Institute of Microelectronic Circuits and Systems, pp. 653-658.

International Search Report and Written Opinion issued Sep. 4, 2012 in connection with PCT/IL2012/000186.

M. S. Humayun et al.: "Visual Perception in a Blind Subject with a Chronic Microelectronic Retinal Prosphesis," Visian Research 43 (2003) pp. 2573-2581.

P. Walter et al.,: "Cortical Activation Via an Implanted Wireless Retinal Prosthesis," IOVS, May 2005, vol. 46, No. 5, pp. 1780-1785.

Invitation to pay additional fees and, where applicable, protest fee, dated Jun. 16, 2014, which issued in the Applicant's PCT Application No. PCT/IB2014/059672.

Examination Report, dated Apr. 16, 2014, which issued in EP11732733.8.

Office Action, dated Nov. 27, 2013, which issued in JP 2011-548843.

Examination Report, dated Feb. 26, 2014, which issued in EP10738277.2.

J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.

An Official Action dated Aug. 12, 2013 and Interview Summary, which issued during the prosecution of U.S. Appl. No. 13/437,310.

Extended European Search Report dated Nov. 19, 2013 which issued during the prosecution of European Patent Application No. 11814197.7.

Partial International Search Report Dated Mar. 31, 2015. (Previously Submitted).

Partial International Search Report dated Mar. 24, 2015. (Previously Submitted).

ISR and the Written Opinion issued on Jun. 30, 2015 in PCT/IB2014/067417.

ISR and the Written Opinion issued on Jun. 30, 2015 in PCT/IB2015/050224.

Office Action that issued on Aug. 20, 2015 in U.S. Appl. No. 14/160,314.

Office Action that issued on Aug. 10, 2015 in U.S. Appl. No. 13/827,919.

Office action that issued on Feb. 5, 2015 in U.S. Appl. No. 14/199,462.

The office action that issued on Feb. 3, 2014 in U.S. Appl. No. 13/683,158.

The office action that issued on Apr. 14 2015 in U.S. Appl. No. 14/018,850.

Invitation to pay additional fees that issued in PCT/IB2014/067417.

Invitation to pay additional fees that issued in PCT/IB2015/050224.

EP search report dated Feb. 20 2015 that issued in EP 12782462.1.

Notice of allowance issued in EP 10738277.2.

* cited by examiner

RETINAL PROSTHESIS

CROSS-REFERENCES TO RELATED APPLICATIONS

The present application is a U.S. national phase of PCT Application No. PCT/IL2010/000097 to Gross et al., filed Feb. 3, 2010, which published as WO/2010/089739 and claims the priority of U.S. patent application Ser. No. 12/368,150 to Gross et al., entitled, "Retinal Prosthesis," filed Feb. 9, 2009 and issued on Apr. 3, 2012 as U.S. Pat. No. 8,150,526 to Gross et al., which is incorporated herein by reference.

FIELD OF EMBODIMENTS OF THE INVENTION

Embodiments of the invention relate generally to implantable medical devices, and specifically to a retinal prosthesis.

BACKGROUND

Retinal malfunction, due to degenerative retinal diseases, is a leading cause of blindness and visual impairment. Implantation of a retinal prosthesis is a technology for restoring some useful vision in individuals suffering from retinal-related blindness.

The retina is a multi-layered light-sensitive structure that lines the posterior, inner part of the eye. The retina contains photoreceptor cells, for example rods and cones, which capture light and convert light signals into neural signals transmitted through the optic nerve to the brain. Rods are responsible for light sensitive, low resolution black and white vision, whereas cones are responsible for high resolution color vision. Most cones lie in the fovea, which defines the center of the retina.

U.S. Pat. No. 6,976,998 to Rizzo et al. describes an externally powered ocular device that is described as a safe and effective retinal prosthesis. The device is described as performing all functions needed of a retinal prosthesis with electronic components that are placed outside the wall of an eye, are powered wirelessly by an external power source, and which provide a patient with a view determined by natural motion of the eye and triggered by natural incident light converging at the retina. An externally powered, light-activated, sub-retinal prosthesis is described in which natural light entering the eye conveys visual details to the sub-retinal prosthesis, while wireless radiofrequency transmission provides the power needed to stimulate the retina, which would be insufficient if it were obtained from the intensity of incoming light alone.

U.S. Pat. No. 4,628,933 to Michelson describes a visual prosthesis for blindness due to retinal malfunction which includes a compact device having a close-packed array of photosensitive devices on one surface thereof. A plurality of electrodes extends from the opposed surface of the device and are connected to the outputs of the photosensitive devices. The device is adapted to be inserted in the posterior chamber of the eye, generally disposed at the focal plane of the optical pathway and impinging on the retina. Anchoring means secure the device with the electrodes operatively connected to the neuron array at the surface of the retina to stimulate the neurons in a pattern corresponding to the illumination pattern of the photosensitive array. The device is powered by externally induced electromagnetic or radio frequency energy, and is encased in a biologically inert housing. An amplifier array may be interposed between the sensing elements and the electrodes to amplify, shape, and time-process the visual signals.

U.S. Pat. No. 6,298,270 to Nisch describes a retina implant that has a substrate with a surface for applying same to a retina. The substrate comprises electrodes for stimulating cells within the retina. The electrodes are provided on the surface and are exposed to visible light impinging on the retina such that stimuli are exerted on the cells by the electrodes. The implant, further, comprises a photovoltaic layer responsive to non-visible light. The stimuli are locally switched utilizing a voltage generated by the photovoltaic layer.

U.S. Pat. No. 6,507,758 to Greenberg et al. describes a device for directly modulating a beam of photons onto the retinas of patients who have extreme vision impairment or blindness. Its purpose is to supply enough imaging energy to retinal prosthetics implanted in the eye which operate essentially by having light (external to the eye) activating photoreceptors, or photo-electrical material. The device is described as providing sufficient light amplification and does it logarithmically. While it has sufficient output light power, the output light level still remains at a described safe level. Most embodiments include balanced biphasic stimulation with no net charge injection into the eye. Both optical and electronic magnification for the image, as for example, using an optical zoom lens, is incorporated. It is described as being otherwise infeasible to zoom in on items of particular interest or necessity. Without proper adjustment, improper threshold amplitudes would obtain, as well as uncomfortable maximum thresholds. Therefore, to adjust for these, a way is described as providing proper adjustment for the threshold amplitudes and maximum comfortable thresholds. Furthermore, to the extent that individual stimulation sites in the retina give different color perceptions, upon stimulation, then colors of the viewed scene is correlated with specific stimulation sites to provide a certain amount of color vision.

U.S. Pat. No. 6,324,429 to Shire et al. describes a chronically-implantable retinal prosthesis for the blind, which is described as restoring some useful vision to patients. The epiretinal devices are described as thin, strong, and flexible and constructed of or encapsulated in known biocompatible materials, which are described as having a long working life in the eye's saline environment. The function of the implants is to electrically stimulate the ganglion cell layer at the surface of the retina using controlled current sources. The implant has planar form and is described as flexible and exceptionally low mass, minimizing patient discomfort and fluid drag. These physical attributes are described as substantially reducing the potential of harm to the most delicate structure of the eye, the retina, and therefore enhance the long term safety and biocompatibility of the device. Since no micro-cables are required to be attached to the device, and its overall form and edges are rounded, the device is described as not stressing the retina during chronic implantation. A provision is also made for nutrients to reach the retinal cells underneath the device to assure their long-term health. The device is meant to process and retransmit images and data to the ganglion cells on the retina surface.

U.S. Pat. No. 5,935,155 to Humayun et al. describes a visual prosthesis comprising a camera for perceiving a visual image and generating a visual signal output, retinal tissue stimulation circuitry adapted to be operatively attached to the user's retina, and wireless communication circuitry for transmitting the visual signal output to the retinal tissue stimulation circuitry within the eye. To generate the visual signal output, the camera converts a visual image to electrical impulses which are sampled to select an image at a given point in time. The sampled image signal is then encoded to allow a pixelized display of it. This signal then is used to modulate a radio frequency carrier signal. A tuned coil pair having a primary and a secondary coil is used to transmit and receive the RF modulated visual signal, which is then demodulated within the eye. The retinal stimulation circuitry includes a decoder for decoding the visual signal output into a plurality of individual stimulation control signals, which are used by current generation circuitry to generate stimulation current signals to be used by an electrode array having a plurality of electrodes forming a matrix. The intraocular components are powered from energy extracted from the transmitted visual signal. The electrode array is attached to the retina via tacks, magnets, or adhesive.

U.S. Pat. No. 7,047,080 to Palanker et al. describes a self-sufficient retinal prosthesis powered by intra-ocular photovoltaic cells illuminated only by ambient light. Photovoltaic cells can be disposed at the periphery of the retina or in the anterior chamber of the eye. An adaptive retinal prosthesis is also provided, such that the number of pixels energized in the prosthesis is selected according to the variable available power from ambient light.

U.S. Patent Application Publication 2006/0282128 to Tai et al. describes intraocular retinal prosthesis systems, and methods for fabricating such prostheses. A prosthesis device includes a cable region that connects an electrode array region with a power and data management region. The electrode array region includes one or more arrays of exposed electrodes, and the power and data management region includes various power and control elements. The power and data management elements, in one aspect, include an RF coil or coils and circuit arrangements and/or chips configured to provide drive signals to the electrodes via a cable and receive power and signals from the RF coil or coils. Each region includes elements fabricated on or in a single polymer layer during the same fabrication process.

U.S. Patent Application Publication U.S. 2007/0191909 to Ameri et al. describes a wide-field retinal prosthesis providing an increased field of vision with a relatively small scleral incision. The retinal prosthesis is described as including a flexible substrate comprising a central member and at least one wing, with an array of electrodes disposed therein that are configured to stimulate the central and peripheral nerves of the retina. The prosthesis can include a desired number of apertures for suitable flexibility.

U.S. Pat. No. 5,597,381 to Rizzo describes a method for epi-retinal implantation of an object into a subject. The method includes rendering the normally transparent cortical vitreous visible and separating at least a portion of a cortical vitreous of the subject away from an adherent retinal surface to form an epi-retinal space between the retina and the separated cortical vitreous material. An object to be implanted may be introduced into the epi-retinal space and the object engaged with a surface of the retina. In preferred embodiments, the object may then be adhered to the surface of the retina. A method for implantation of a neural contact structure for contact with neural tissue, for example, neural tissue of the retina within which are ganglion cells to be electrically stimulated is also described. The contact structure comprises a first portion for attachment to a first bodily location, such as the inner surface of the retina, and a second portion interconnected with the first portion via an interconnection and being held in contact with the neural tissue. The interconnection exhibits a weak restoring force which in conjunction with the geometry of the second portion provides a preselected desired pressure of contact against the neural tissue. As adapted for the retina, the interconnection exhibits a weak restoring force developed in response to curvature of the interconnection along the inner radius of the retina.

U.S. Pat. No. 6,368,349 to Wyatt et al. describes a neural prosthesis for implantation within an eye. The prosthesis includes a foldable substrate and at least one electronic component supported by the substrate. At least one microchannel is disposed within the substrate. Upon inflation, the foldable substrate is described as unfolding to provide for close contact of the electronic component with neural tissue, thus facilitating surgical implantation through a narrow incision, yet allowing the unfolded device to cover a sufficiently large portion of the patient's retina to provide useful vision.

The following references may be of interest:
U.S. Pat. Nos. 2,721,316
2,760,483
4,272,910
4,551,149
4,601,545
4,664,117
4,969,468
5,016,633
5,024,223
5,108,427
5,109,844
5,147,284
5,159,927
5,397,350
5,411,540
5,476,494
5,526,423
5,575,813
5,674,263
5,800,533
5,800,535
5,836,996
5,837,995
5,865,839
5,873,901
5,895,415
5,944,747
6,032,062
6,230,057
6,389,317
6,442,431
6,611,716
6,658,299
6,755,530
7,003,354
7,006,873
7,027,874
7,031,776
7,037,943
7,103,416
7,139,612
7,162,308
7,251,528
7,321,796
PCT application WO 2007/09539
Zrenner E., 2002. "Will retinal implants restore vision?" Science 295(5557), pp. 1022-1025.

SUMMARY OF EMBODIMENTS OF THE INVENTION

In some applications of the present invention, apparatus is provided for restoring at least partial vision in a subject suffering from a retinal disease. The apparatus comprises an external device, comprising a mount that is placed in front of the subject's eye. The mount may be, for example, a pair of eyeglasses. The external device further comprises a power source, for example a laser that is coupled to the mount and is configured to emit radiated energy that is outside the visible range that is directed toward the subject's eye.

The apparatus additionally comprises an intraocular device, which is implanted entirely in the subject's eye. The intraocular device is configured to be implanted in the subject's eye in either an epi-retinal or a sub-retinal position. The intraocular device comprises a thin and typically flexible silicon array. The intraocular device comprises an energy receiver, which receives the radiated energy from the power source and generates a power signal to power other components of the intraocular device. The intraocular device further comprises an array, each unit of the array comprising a photosensor and a stimulating electrode. Each photosensor detects photons and generates a photosensor signal responsively to the photons. The photosensor signal is passed to driving circuitry, which uses energy from the energy receiver to drive the electrodes to apply currents to the retina. Stimulation of the retina elicits action potentials in the retinal ganglion cells, restoring some vision by activating the intact mechanisms of the eye.

There is therefore provided, in accordance with some applications of the invention, an apparatus including:

an external device including:
  a mount, configured to be placed in front of an eye of a subject;
  a laser coupled to the mount and configured to emit radiation that is outside of 380-750 nm; and
  a partially-transparent mirror coupled to the mount; and
an intraocular device configured to be implanted entirely in the subject's eye, the intraocular device including:
  an energy receiver, configured to receive the radiation from the laser and to generate a voltage drop in response thereto;
  a plurality of stimulating electrodes;
  a plurality of photosensors, each photosensor configured to detect photons and to generate a signal in response thereto; and
  driving circuitry, coupled to the energy receiver and to the photosensors, and configured to receive the signals from the photosensors and to utilize the voltage drop to drive the electrodes to apply currents to a retina of the eye in response to the signals from the photosensors.

In some applications, the laser is configured to emit the light at 790-850 nm.

In some applications, the laser is configured to emit the light at 250-380 nm.

In some applications, the energy receiver is configured to receive light at 790-850 nm and to generate the voltage drop in response thereto.

In some applications, the energy receiver is configured to receive light at 250-380 nm and to generate the voltage drop in response thereto.

In some applications, the photosensors are generally insensitive to the energy from the laser.

In some applications, photosensors are generally sensitive to visible light.

In some applications, the energy receiver is configured to receive visible and non visible light, and to generate the voltage drop in response thereto.

In some applications, the intraocular device includes a filter configured to allow transmission to the photosensors of visible light only.

In some applications, the intraocular device includes a plurality of microlenses coupled to the energy receiver, facilitating refraction of visible light toward the photosensors.

In some applications, the intraocular device includes extending elements configured to provide anchoring of the intraocular device to the eye of the subject.

In some applications, the intraocular device includes extending elements to facilitate dissipation of heat away from at least the energy receiver.

In some applications, the electrodes include bipolar nanotube electrodes.

In some applications, the electrodes include monopolar nanotube electrodes.

In some applications, the electrodes include needle electrodes having exposed tips.

In some applications, the plurality of stimulating electrodes includes at least 100 electrodes.

In some applications, the intraocular device is configured to be implanted in an epi-retinal position.

In some applications, the intraocular device is configured to be implanted in a sub-retinal position.

In some applications, the apparatus includes a control element configured to receive an input from the subject, the external device is configured to modulate the energy emitted from the laser in response to the input, and the driving circuitry is configured to regulate a parameter of operation of the driving circuitry in response to the modulation of the energy emitted from the laser.

In some applications, the driving circuitry is configured to control an amount of stimulation per unit time applied by the electrodes, by the regulating of the parameter by the driving circuitry.

In some applications, the driving circuitry is configured to control an amplitude of the currents applied by the electrodes, by the regulating of the parameter by the driving circuitry.

In some applications, the driving circuitry is configured to control a sensitivity of the photosensors, by the regulating of the parameter by the driving circuitry.

In some applications, the external device includes a sensor coupled to the mount, configured to detect when an eyelid of the subject is closed, and the laser is configured to discontinue emission of the radiation when the eyelid is closed.

In some applications, the mount includes a filter configured to prevent transmission to the photosensors of ambient non-visible light.

In some applications, the filter includes a Schott filter.

In some applications, the driving circuitry is disposed in a single area of the intraocular device, and is configured to drive all of the electrodes.

In some applications, the apparatus includes a plurality of driving circuitries, each driving circuitry configured to drive a respective subset of electrodes.

In some applications, the plurality of driving circuitries includes 10-300 driving circuitries.

In some applications, the plurality of driving circuitries includes 300-3000 driving circuitries.

There is further provided in accordance with some applications of the invention apparatus, including:

an external device, including:
  a mount, configured to be placed in front of an eye of a subject; and
  a laser coupled to the mount and configured to emit radiation that is outside of 380-750 nm; and
an intraocular device configured to be implanted entirely in the subject's eye, the intraocular device including:

an energy receiver, configured to receive the radiation from the laser and to generate a voltage drop in response thereto;

a plurality of stimulating electrodes;

a plurality of photosensors, each photosensor configured to detect photons and to generate a signal in response thereto; and driving circuitry, coupled to the energy receiver and to the photosensors, and configured to receive the signals from the photosensors and to utilize the voltage drop to drive the electrodes to apply currents to a retina of the eye in response to the signals from the photosensors, and the external device is configured to modulate the radiation emitted from the laser, and the driving circuitry is configured to regulate a stimulation parameter of operation of the driving circuitry in response to the modulation of the radiation emitted from the laser.

In some applications, the driving circuitry is configured to drive the electrodes to apply the currents in pulses of current, and the stimulation parameter is selected from the group consisting of: a number of the pulses, a frequency of the pulses, a duration of each pulse, and a pulse repetition interval of the pulses.

There is additionally provided in accordance with some applications of the invention, a method for supplying power to a retinal implant, including:

emitting radiation from a laser, in a direction that is not toward the implant; and receiving the radiation from the laser, by the implant.

In some applications, emitting the radiation comprises causing the radiation to be redirected toward the implant by a partially-transparent mirror.

There is yet further provided in accordance with some applications of the invention, a method for modulating stimulation parameters of an implant configured for implantation in a subject, the method including:

emitting laser radiation, from a laser to the implant;

receiving an input from the subject, and in response to receiving the input from the subject, modulating the radiation emitted from the laser; and regulating a stimulation parameter of driving circuitry of the implant in response to the modulation of the radiation emitted from the laser.

In some applications, regulating the stimulation parameter includes:

driving currents into electrodes of the implant in pulses; and in response to the modulation of the radiation, regulating at least one parameter selected from the group consisting of a number of the pulses, a frequency of the pulses, a duration of each pulse, and a pulse repetition interval of the pulses.

The present invention will be more fully understood from the following detailed description of embodiments thereof, taken together with the drawing, in which:

DETAILED DESCRIPTION OF EMBODIMENTS

Figure 1:
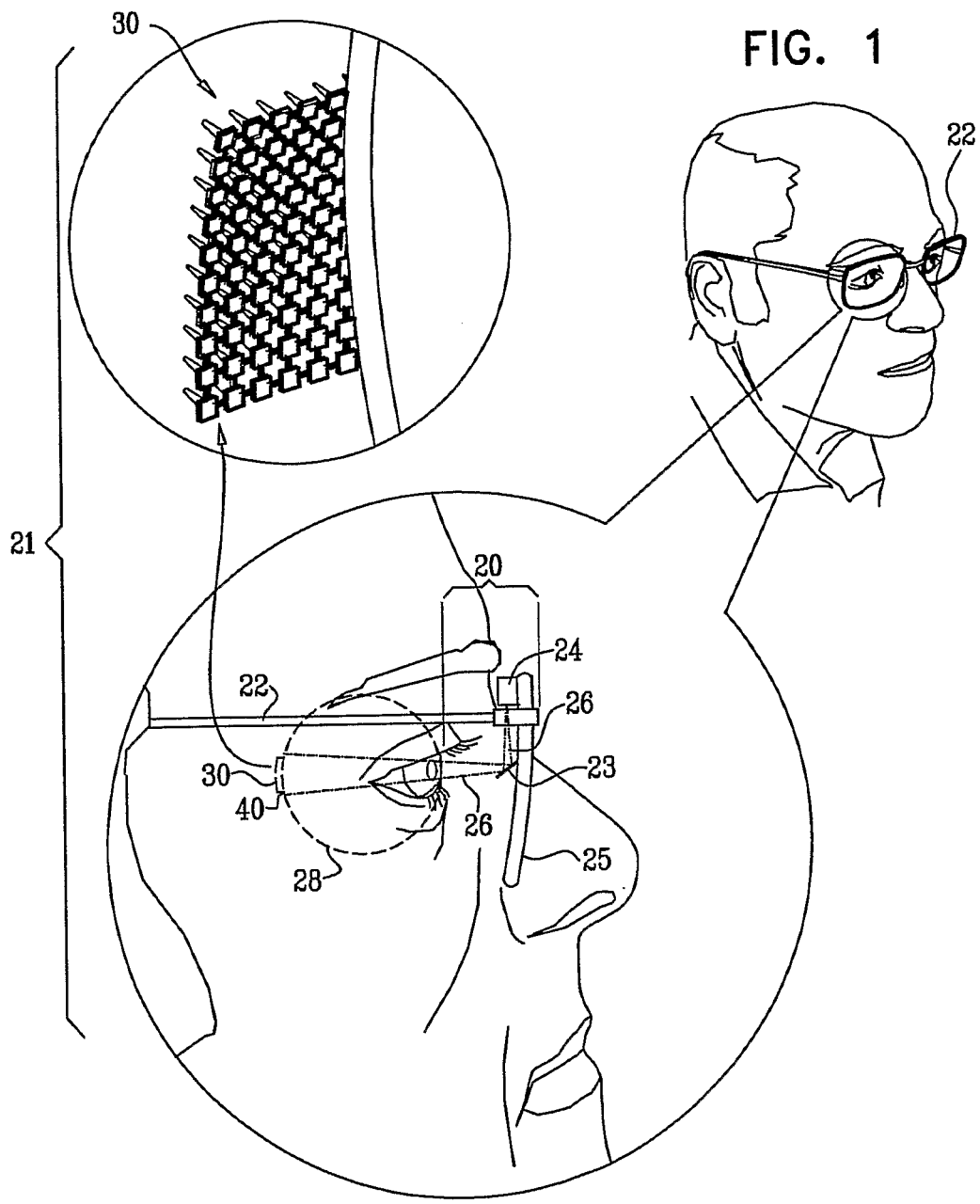
FIG. 1 is a schematic illustration of apparatus for restoring at least partial vision in a subject, in accordance with some applications of the present invention.

FIG. 1 is a schematic illustration of apparatus 21 for restoring at least partial vision in a subject suffering from retinal malfunction, in accordance with some applications of the present invention. Apparatus 21 comprises an external device 20 comprising a mount 22, which is typically a pair of eyeglasses, and is placed in front of a subject's eye 28. External device 20 further comprises a power source, for example a laser 24, which is coupled to the mount and is configured to emit radiated energy 26, which is outside the visible range, that is directed toward the subject's eye 28. Laser 24 is shown coupled to the inner part of lens 25 by way of illustration and not limitation. Laser 24 may be coupled to other members of mount 22 for example, to the arm of the eyeglasses.

Apparatus 21 additionally comprises an intraocular device 30, which is implanted entirely in eye 28. Intraocular device 30 comprises a small e.g., 3-6 mm in diameter, thin e.g., less than 1 mm thick, and typically flexible silicon array.

Retinal implants are generally configured to be implanted in either a sub-retinal or an epi-retinal position. Epi-retinal arrays are typically implanted onto the retinal surface that separates the retinal neural layer from the vitreous body of the eye's posterior chamber. Epi-retinal implants are typically described as having no light sensitive areas and therefore receive electrical signals from a distant camera and processing unit outside of the subject's body. These described epi-retinal implants are coupled to the ganglion cells and their axons, and therefore directly simulate the ganglia (Zrenner 2002). In contrast, sub-retinal implants are typically implanted under the retina between the pigment epithelial layer and the outer layer of the retina which contains the photoreceptor cells. Sub-retinal implants typically stimulate the remaining neural cells of the retina (Zrenner 2002).

Intraocular device 30, in accordance with some applications of the present invention, is configured to be implanted in either the epi-retinal or the sub-retinal space of eye. In both locations, intraocular device 30 receives visible light emanating from objects. The visible light strikes photosensors of the intraocular device, which generate a signal via intermediate circuitry causing electrodes on the intraocular device to stimulate retinal sensory neurons (for example the bipolar cells), resulting in the sensation of an image. Stimulation of the bipolar cells activates and utilizes the intact optics and processing mechanisms of the eye.

In some applications of the present invention, intraocular device 30 comprises needle electrodes with exposed tips configured to extend through the ganglion cells to directly contact and stimulate the bipolar cell layer, which in turn stimulates the ganglion cells, when intraocular device 30 is implanted in an epi-retinal position. The ganglion cells, whose axons form the optic nerve, further transmit the visual information to the brain. Apparatus 21 does not comprise a camera, and intraocular device does not receive image data, but rather utilizes the intact optics and processing mechanisms of eye.

In some applications of the present invention, intraocular device 30 is implanted in the subject's eye in a sub-retinal position. As described hereinabove, intraocular device 30 receives visible light emanating from objects. The visible light strikes the photosensors of the intraocular device, which generates a signal to drive electrodes 38 of the intraocular device. In applications in which intraocular device 30 is implanted in the sub-retinal space, the electrodes of intraocular device 30 are positioned in a suitable orientation allowing the electrodes to directly contact and stimulate the bipolar cells of the retina, which in turn stimulate the ganglion cells, resulting in image resolution. Similar to the implantation of intraocular device 30 in the epi-retinal position, implantation in the sub-retinal position also utilizes the intact optics and processing mechanisms of eye 28.

Figure 2:
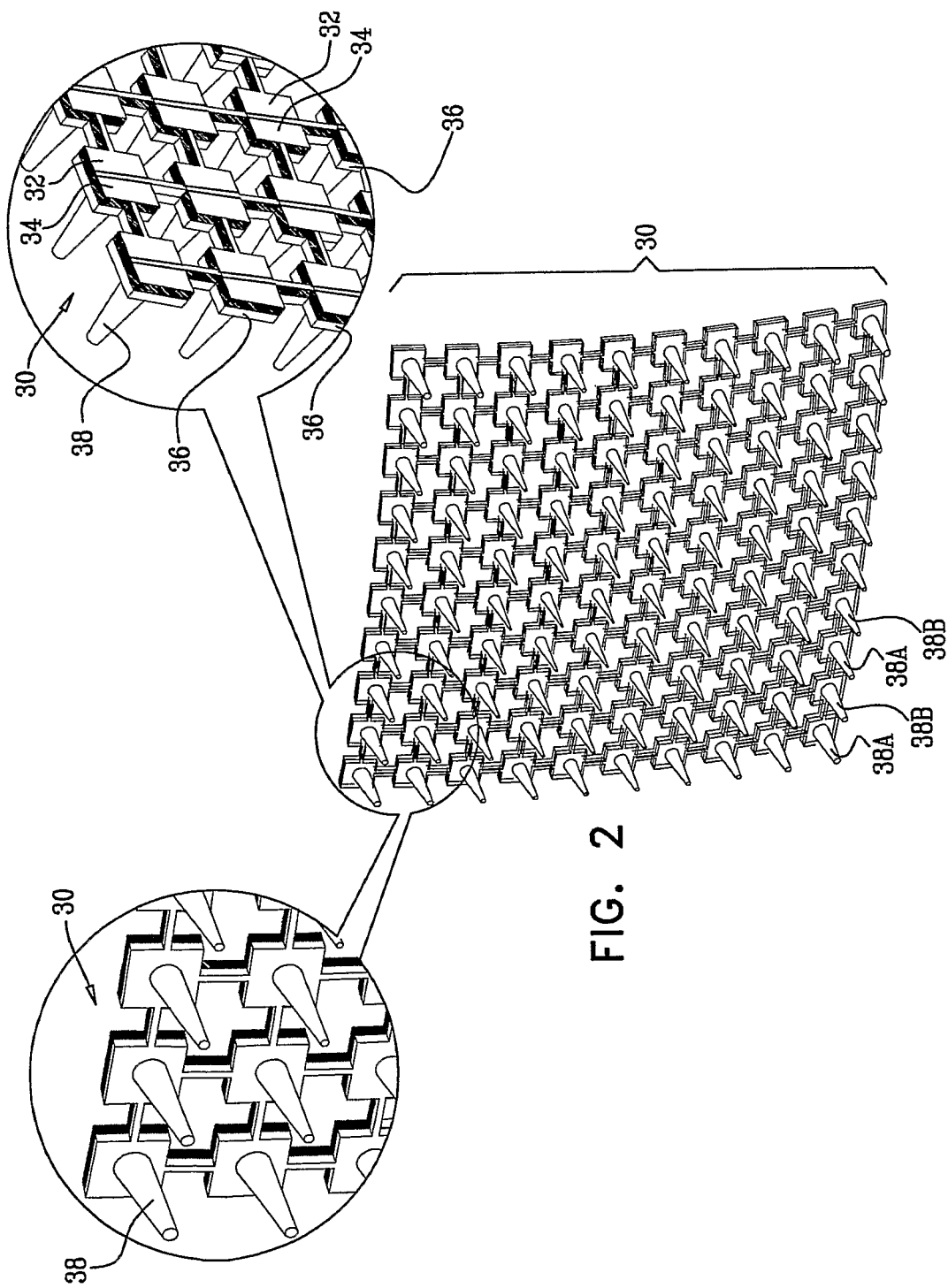
FIG. 2 is a schematic illustration of an intraocular device, in accordance with some applications of the present invention.

FIG. 2 is a schematic illustration of intraocular device 30, in accordance with some applications of the invention. Intraocular device 30 comprises an array, each unit of the array comprising an energy receiver 32 which receives radiated energy 26 from laser 24 of external device 20 (FIG. 1). Energy receiver 32 generates a power signal to power other components of intraocular device 30. Alternatively, a single energy receiver 32 (or a small number of receivers 32) is configured to receive radiated energy 26 from laser 24, to power the components of the entire intraocular device 30. Each unit of the intraocular device 30 further comprises a photosensor 34, a stimulating electrode 38, and driving circuitry 36. A signal generated by photosensor 34 is passed to driving circuitry 36, which utilizes energy from the energy receiver 32 to drive electrode 38 to stimulate the retina. Alternatively, some or all of electrodes 38 are driven by driving circuitry 36 in a single area of intraocular device 30 (rather than by discrete driving circuitry physically located next to each electrode). Accordingly, for some applications, intraocular device 30 may comprise a plurality of driving circuitries, e.g., 10-3000 driving circuitries, each driving circuitry being configured to drive a respective subset of electrodes.

It is noted that FIG. 2 shows intraocular device 30 configured for epi-retinal implantation. In another application, electrodes 38 extend from intraocular device 30 in the direction of the pupil, and intraocular device 30 is implanted sub-retinally (configuration not shown).

Reference is now made to FIGS. 1 and 2. External device 20 further comprises ophthalmoscope functionality, including a partially-transparent (e.g., half-silvered) mirror 23 coupled to a lens 25 of mount 22. The partial transparency of mirror 23 allows energy from laser 24 to reach energy receiver 32 without the physical apparatus of laser 24 occluding vision. Additionally, light from the environment which forms images on the array of photosensors 34 is able to pass through partially-transparent mirror 23. The use of ophthalmoscope functionality as described further allows the use of a large diameter laser beam (e.g., 5-20 mm, such as 5-10 mm), which provide high total radiated energy 26, while minimizing the density of the beam at the retina. If such a laser beam originated from a laser mounted on lens 25 itself, it would interfere with vision by blocking incoming light from the environment.

Figure 3:
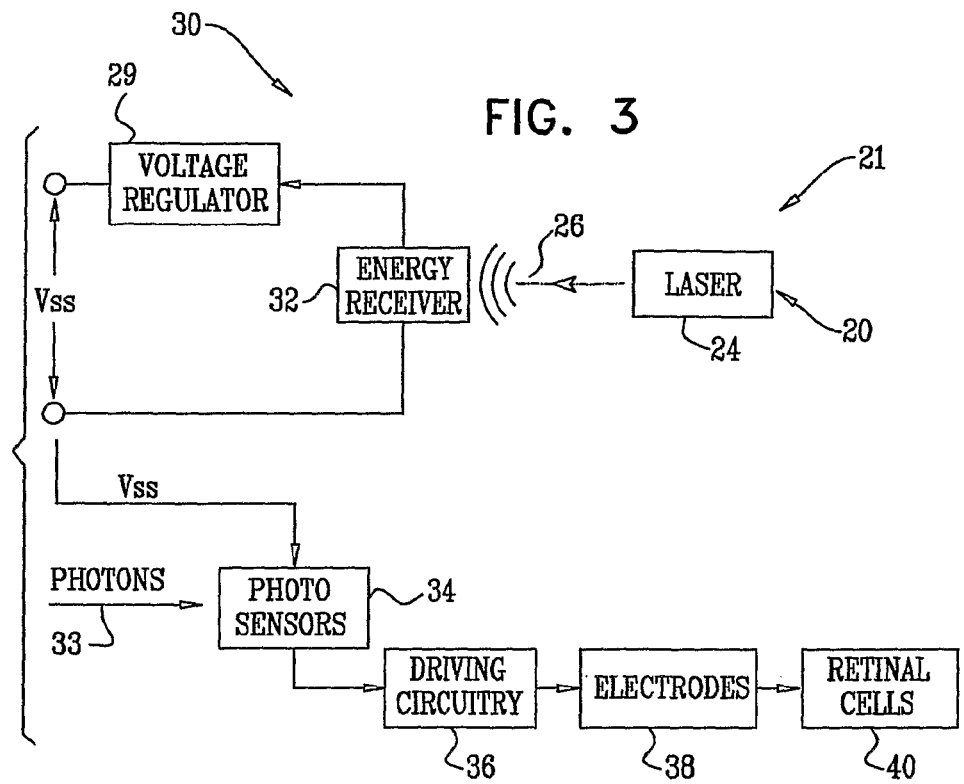
FIG. 3 is a block diagram of the transmission of energy in the apparatus for restoring vision, in accordance with some applications of the present invention.

FIG. 3 is a block diagram of apparatus 21, in accordance with some applications of the present invention. External device 20 (FIG. 1) comprises laser 24, which emits radiated energy 26 to power components of intraocular device 30. Radiated energy 26 transmitted to the intraocular device 30 is received by energy receiver 32. Energy receiver 32 typically comprises a voltage regulator 29 configured to maintain a constant voltage level to power the components of intraocular device 30. Intraocular device 30 further comprises photosensors 34 configured to detect photons 33 and generate a photosensor signal responsively to the photons 33. The photosensor signal is transmitted to driving circuitry 36, which drives the electrode 38 to apply currents to retinal cells 40.

Figure 4:
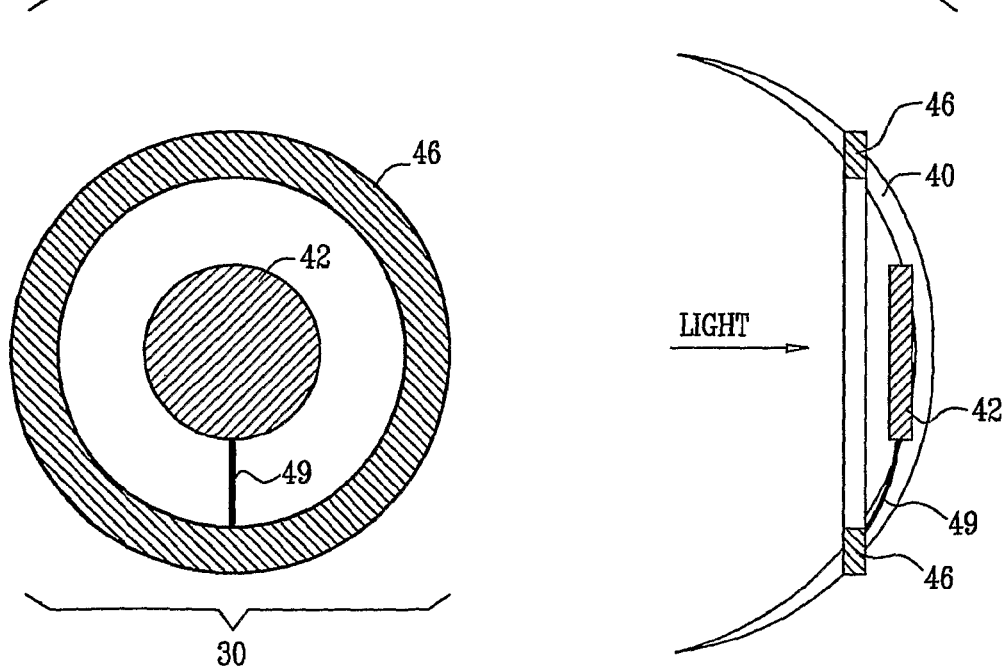
FIG. 4 is a schematic illustration of the intraocular device, in accordance with some applications of the present invention.

FIG. 4 is a schematic illustration of intraocular device 30, in accordance with some applications of the present invention. Intraocular device 30 comprises a generally small array 42, e.g., 3-6 mm in diameter, and 1 mm thick. The array is surrounded by an additional toroidal array 46 that is physically associated with the rod cells area of the retina 40, providing some degree of scotopic vision and/or wider-field vision. Arrays 42 and 46, which generally function in a similar manner, are coupled by a multi-wire element 49.

Figure 5:
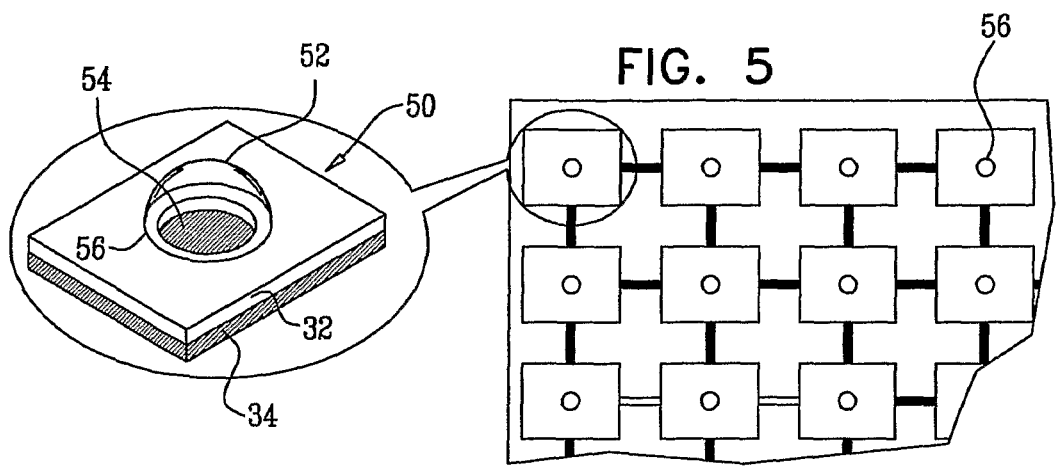
FIG. 5 is a schematic illustration of an energy receiver-photosensor unit, in accordance with some applications of the present invention.

FIG. 5 is a schematic illustration of an energy receiver-photosensor unit 50, in accordance with some applications of the present invention. Each energy receiver 32 has a hole 56 passing therethrough, through which light passes to strike a corresponding photosensor 34 located under the hole 56. The energy-receiving portion of each energy receiver 32 is typically 50-250 um across (e.g., 75-150 um across), and the diameter of each hole is typically 10-120 um, e.g., 20-60 um. The energy-receiving area of each energy receiver is typically about 5-10 times greater than the area of each hole.

Photosensor 34 typically comprises a filter 54 allowing transmission of visible light, and blocking transmission of light emitted by laser 24. As appropriate, filter 54 may allow substantially only visible light, or visible light and some non-visible light (e.g., near infrared) to strike the photosensor. Energy receiver 32 is typically optimized to transduce light of the wavelength of laser 24 into electricity, although it may alternatively be sensitive to a wider range of wavelengths, such as to both visible and non-visible light.

For some applications, energy receiver-photosensor unit 50 comprises a microlense 52, which facilitates refraction of light toward photosensor 34 that would otherwise strike energy receiver 32. Accordingly, microlense 52 comprises prism functionality, allowing for differential refraction of visible light and non-visible (power transmitting) light, such that the non-visible light lands on the energy receiver to power intraocular device 30, while the visible light is refracted toward photosensors 34 which generate a signal in response to visible light photons. This provides some "averaging" of the light striking each photosensor, by combining that light with light that would otherwise strike the implant near the photosensor, thus mitigating the sensation of spaced individual pixels of light that may be sensed by a user with a retinal prosthesis. Using this technique, a slightly blurred image is intentionally formed, in which the extent of stimulation applied by a given electrode to the retina represents not only the light striking the very-small area of the corresponding photosensor, but also light that strikes the surrounding area under the microlense. (It is to be understood that in some embodiments, such a microlense is not provided.)

Figure 6A:
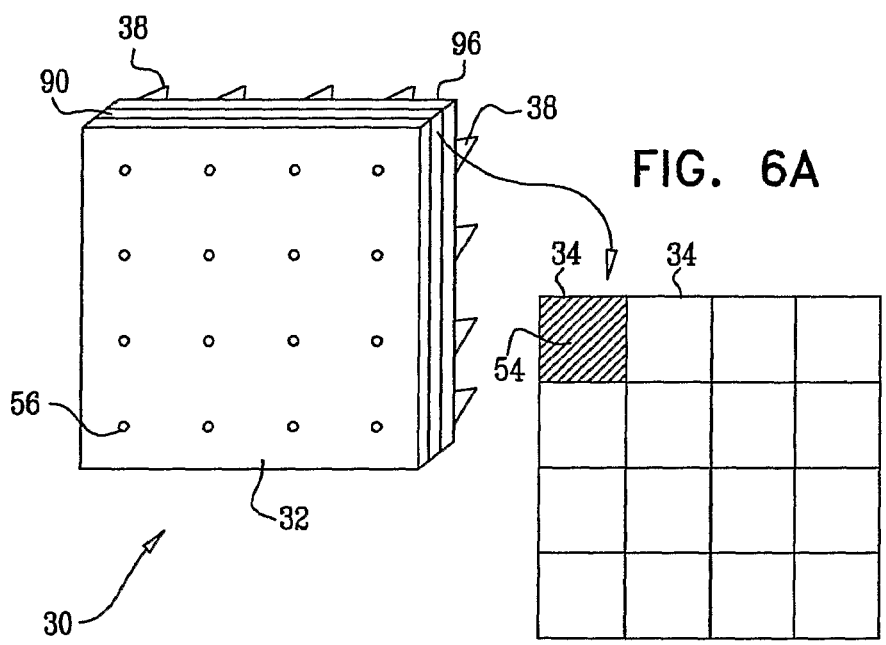
FIGS. 6A and 6B are schematic illustration of layered structures of the intraocular device, in accordance with respective applications of the invention.

Reference is made to FIG. 6A, which is a schematic illustration of intraocular device 30, in accordance with some applications of the invention. In some embodiments of the present invention intraocular device 30 is assembled as a triple-layered device, comprising an energy receiving 32 top layer, a photosensor middle layer 90 and a driving circuitry layer 96, coupled to electrodes 38. Energy receiving 32 layer is configured to receive radiated laser energy, in order to power intraocular device 30. Additionally, energy receiving 32 layer is shaped to define a plurality of holes 56 passing therethrough, through which light passes to strike photosensor layer 90 located under the holes 56. The middle layer of intraocular device 30 comprises individual photosensor units 34. Each photosensor unit typically comprises a filter 54 allowing transmission of visible light, and blocking transmission of light emitted by the laser. Visible light striking photosensor units 34 generates a current which is processed in the bottom, driving circuitry layer 96, of intraocular device 30. Driving circuitry layer 96 is coupled to electrodes 38 that stimulate the retinal cells to generate an image and restore vision.

It is noted that FIG. 6A shows intraocular device 30 configured for epi-retinal implantation. In another application, electrodes 38 extend from the energy receiving 32 layer, and intraocular device 30 is implanted sub-retinally (configuration not shown).

Figure 6B:
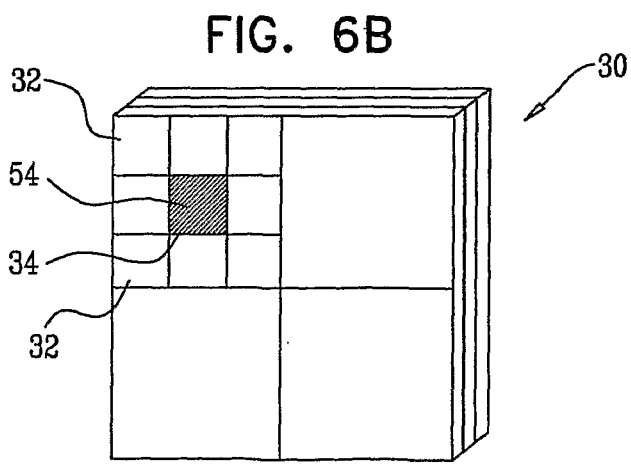

Reference is made to FIG. 6B, which is a schematic illustration of intraocular device 30, in accordance with another application of the invention. In this application, the top layer of intraocular device 30 comprises both energy receivers 32 and photosensors 34. For example, the top layer of intraocular device 30 may comprise an array divided into sub-arrays. Each sub-array is further divided into (for example) nine units each. The central unit of each sub-array comprises a photosensor 34, typically comprising a filter 54 which passes visible light. The surrounding units in each sub-array are energy receiving units 32, receiving radiated laser energy to power intraocular device 30. As appropriate, electrodes 38 may be coupled to the top layer, for sub-retinal implantation, or to the bottom layer, for epi-retinal implantation.

Typically, apparatus 21 activates and utilizes the intact optic mechanisms, natural movements, and focusing of eye 28. Furthermore, intraocular device 30 is typically a small and flexible device e.g., 3-6 mm in diameter, and less than 1 mm thick, implanted in a either an epi-retinal or a sub-retinal position, and powered by an external power source e.g., a laser. Therefore, intraocular device 30 is wireless, does not comprise bulky components, and does not require power-consuming internal microcontrollers. Additionally, energy receiver 32, receiving radiated energy 26, for example laser energy, is typically fine-tuned to match a specific laser wavelength (for example an IR wavelength such as 790-850 nm, or a suitable UV wavelength). Therefore, a substantial portion of radiated energy 26 is utilized to power electrodes 38, allowing for an increased number of electrodes 38 and thereby resulting in enhanced image resolution. For example, if a total of 35 mW of laser energy reaches intraocular device 30, this provides an estimated 14 mW of usable electricity (assuming an approximate 40% efficiency rate).

For some applications electrodes 38 are bipolar or alternatively monopolar nanotube electrodes coated with carbon nanotubes.

The number of electrodes per array typically ranges between 100-10,000 electrodes. In some applications, a relatively smaller number of electrodes (e.g., 100-1,000) are in generally continuous use, while a higher number of electrodes (e.g., 1,000-10,000), which are not continuously activated, can enable the subject to temporarily increase resolution at the cost of heating of the eye for several seconds. Additionally or alternatively, intraocular device 30 comprises interleaved arrays of electrodes 38*a* and 38*b*, which are activated separately, thus stimulating adjacent retinal sites and generating the illusion of higher-resolution of an actual image.

In some applications of the present invention, intraocular device 30 comprises support elements extending away from the retina. Support elements are typically composed of biocompatible materials (for example, PtIr), possibly insulated with an additional biocompatible material. The support elements aid in anchoring implanted intraocular device 30 to the subject's eye 28. Additionally or alternatively, the support elements contribute to enhanced dissipation of heat, preventing local overheating of eye 28. The total volume of support elements is typically similar to the volume of intraocular device 30 (for example, 25 mm3), allowing for efficient heat dissipation.

In some applications of the present invention, external device 20 comprises a sensor coupled to mount 22. Apparatus 21 is configured to detect blinking, and to not transmit power to intraocular device 30 when the subject's eyelid is closed. The sensor is configured to detect the rapid closing and opening of the eyelid of the subject, and to signal to laser 24 to cease emitting radiation 26 to the eye when the eyelid of the subject is closed. For some applications, the sensor comprises an electromyography (EMG) sensor or a camera with image processing functionality to determine when the eye is closed. For some applications, the sensor comprises a light sensor coupled to a light emitting diode (LED), which is located adjacent to laser 24. The LED emits light which passes through partially-transparent mirror 23 and is directed towards the subject's eye 28. The amount (or another parameter) of reflected LED light from the eye changes as a result of the subject's blinking. These changes in the amount of the reflected light are detected by the light sensor, which causes laser 24 to discontinue emitting radiation 26 to eye 28 when the eyelid of the subject is closed. Alternatively, for some applications, mount 22 comprises a light sensor located in proximity to laser 24. The light sensor detects reflected laser light, and laser 24 discontinues emitting radiation 26 to the eye when the eyelid of the subject is closed.

In some embodiments of the present invention, apparatus 21 is configured to provide the subject with audio feedback advising the subject to aim eye 28 so that radiation from laser 24 reaches intraocular device 30. Accordingly, for some applications, external device 20 comprises a light sensor coupled to laser 24, configured to detect the amount of reflected laser light and to trigger an audio signal to the subject based on changes in the reflected light indicative of the laser light not being directed toward intraocular device 30. For example, a different portion of the laser light is absorbed by intraocular device 30 when laser 24 is properly aimed, compared to when the laser beam is diverted and not directed at eye 28. In this latter case, the audio feedback signal is triggered.

For some applications, in addition to supplying power to device 30, radiation 26 emitted by laser 24 is used to regulate operation of intraocular device 30. In some applications of the present invention, external device 20 comprises a control element (e.g., a dial, switch, or button) coupled to mount 22, allowing the subject to interactively control the intensity of the signal applied to the retina and/or the sensitivity of photosensors 34 to received light, and/or another system parameter. For example, if the subject determines that the overall stimulation being applied by intraocular device 30 to the retina is too strong, then he can adjust a setting on the control element to reduce the stimulation strength. Similarly, if he determines that the sensitivity of photosensors 34 is too high (e.g., resulting in the entire array of electrodes activating the retina), then he can adjust another setting on the control element to reduce the sensitivity. In response to the subject's input, control element 27 modulates radiation 26 emitted by laser 24 to regulate operating parameters of intraocular device 30. An example of a suitable modulation protocol includes a first train of six short pulses from laser 24, indicating that stimulation intensity is going to be changed, followed by a train of between one and ten longer pulses indicating a subject-selected desired level of stimulation intensity. To change sensitivity, a first train of six long pulses is emitted from laser 24, followed by a train of between one and ten longer pulses indicating a subject-selected desired level of sensitivity. A person of ordinary skill in the art will appreciate that other encoding protocols may be used, as well.

Alternatively, for some applications, regulation of the intensity of the signal applied to the retina and/or the sensitivity of photosensors 34 to received light, and/or another system parameter, is regulated by intraocular device 30. The degree of retinal stimulation applied by each unit of intraocular device 30 is dictated by the light received by that unit. Intraocular device 30 is configured to sense the amount of ambient light which is received by photosensors 34, and in response, to alter the signal which is applied to the retina. For example, based on the amount of ambient light which lands on a given photosensor, intraocular device 30 is configured to modulate the signal by adjusting photosensor output and/or driving circuitry parameters such as gain and/or DC offset, allowing for increased sensitivity of apparatus 21. Modulation of the signal applied to the retina is typically controlled by varying pulse parameters, e.g., of number of pulses, pulse repetition intervals, pulse frequency, and pulse duration. That is, electrodes 38 drive currents into the retinal neurons using pulse parameters selected in response to the amount of light received by the photosensor. Such modulation of photosensor pulse signals to the driving circuitry facilitates regulation of intraocular device 30, for example, in response to changing levels of ambient light.

Similarly, the threshold for transmission of a photosensor signal to the driving circuitry i.e., the sensitivity of photosensors 34, is regulated by the amount of ambient light reaching the photosensors. For some applications, the amount of ambient light that lands on the array of photosensors 34 is used to govern the duration of a sensing period of each photosensor, i.e., the amount of time in which the photosensor receives photons before the driving circuitry drives electrodes 38 to drive currents into retinal tissue (e.g., 10 ms-100 ms). Thus, for example, the sensitivity of each photosensor may be increased over the course of several seconds, if the subject enters a dark room.

Typically, regulation of system parameters of intraocular device 30, by laser and/or by device 30 itself, is achieved by varying selected pulse parameters, e.g., the number of pulses, pulse repetition intervals, pulse frequency, and/or pulse duration.

As described hereinabove, in addition to powering intraocular device 30, in some applications, radiation 26 emitted by laser 24 is additionally used to regulate operating parameters of intraocular device 30. Laser 24 is typically configured to emit energy 26 that is outside the visible range and is directed toward the subject's eye 28. For example, the radiation may be infrared (IR) radiation. For such applications, lens 25 of eyeglasses 22 may comprise an optical filter, e.g., a Schott filter. The filter is configured to filter IR radiation, thereby reducing the amount of ambient IR radiation that reaches photosensors 34 and may interfere with the IR radiation emitted by laser 24. Radiated energy 26 is generally not affected by the filter placed on lens 25, as laser 24 is typically coupled to the inner part of lens 25 as shown in FIG. 1.

In some applications of the present invention, activation of apparatus 21 is regulated by a threshold to prevent saturation (i.e., over-stimulation of the retina by intraocular device 30).

It is to be noted that a plurality of intraocular devices 30 may be implanted in discrete locations in tissue of the retina, either arranged in an array, or, for example, pseudo-randomly. Typically, intraocular device 30 is wireless and does not comprise bulky components, facilitating implantation of several intraocular devices 30 in the retina of a subject.

For some applications, techniques described herein are practiced in combination with techniques described in one or more of the following references, which are incorporated herein by reference:
  U.S. Pat. No. 4,628,933 to Michelson
  U.S. Pat. No. 5,597,381 to Rizzo
  U.S. Pat. No. 5,935,155 to Humayun et al.
  U.S. Pat. No. 6,298,270 to Nisch
  U.S. Pat. No. 6,324,429 to Shire et al.
  U.S. Pat. No. 6,368,349 to Wyatt et al.
  U.S. Pat. No. 6,507,758 to Greenberg et al.
  U.S. Pat. No. 6,976,998 to Rizzo et al.
  U.S. Pat. No. 7,047,080 to Palanker et al.
  U.S. Patent Application Publication 2006/0282128 to Tai et al.
  U.S. Patent Application Publication U.S. 2007/0191909 to Ameri et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
    an external device, comprising:
        a mount, configured to be placed in front of an eye of a subject; and
        a power source coupled to the mount and configured to emit radiation that is outside of 380-750 nm; and
    an intraocular device configured to be implanted entirely in the subject's eye, the intraocular device comprising:
        an energy receiver, configured to receive the radiation from the power source and to generate a voltage drop in response thereto;
        a plurality of stimulating electrodes;
        a plurality of photosensors, each photosensor configured to detect photons and to generate a signal in response thereto; and
        driving circuitry, coupled to the energy receiver and to the photosensors, and configured to receive the signals from the photosensors and to utilize the voltage drop to drive the electrodes to apply currents to a retina of the eye in response to the signals from the photosensors,
    wherein the external device is configured to modulate the radiation emitted from the power source using an encoding protocol such that pulses of the radiation are encoded by the encoding protocol, and
    wherein the driving circuitry is configured to regulate a parameter of operation of the driving circuitry in response to the modulation of the radiation emitted from the power source, and
    wherein the driving circuitry is configured to control a sensitivity of the photosensors, by the regulating of the parameter by the driving circuitry.

2. The apparatus according to claim 1, further comprising a partially-transparent mirror coupled to the mount.

3. The apparatus according to claim 1, wherein the power source comprises a laser.

4. The apparatus according to claim 1,
    wherein the power source is configured to emit the radiation at 790-850 nm, and wherein the energy receiver is configured to receive radiation at 790-850 nm and to generate the voltage drop in response thereto.

5. The apparatus according to claim 1, wherein the photosensors are generally insensitive to the radiation from the power source.

6. The apparatus according to claim 1, wherein the photosensors are generally sensitive to visible light.

7. The apparatus according to claim 1, wherein the intraocular device comprises a filter configured to allow transmission to the photosensors of visible light only.

8. The apparatus according to claim 1, wherein the intraocular device further comprises extending elements to facilitate dissipation of heat away from at least the energy receiver.

9. The apparatus according to claim 1, wherein the electrodes comprise needle electrodes having exposed tips.

10. The apparatus according to claim 1, wherein the plurality of stimulating electrodes comprises at least 100 electrodes.

11. The apparatus according to claim 1, wherein the intraocular device is configured to be implanted in an epiretinal position.

12. The apparatus according to claim 1, further comprising a control element coupled to the mount and configured to receive an input from the subject, and wherein the external device is configured to modulate the radiation emitted from the power source in response to the input.

13. The apparatus according to claim 1, wherein the driving circuitry is configured to control an amount of stimulation per unit time applied by the electrodes, in response to the modulation of the radiation emitted from the power source.

14. The apparatus according to claim 1, wherein the driving circuitry is configured to control an amplitude of the currents applied by the electrodes, in response to the modulation of the radiation emitted from the power source.

15. The apparatus according claim 1, wherein the mount further comprises a filter configured to prevent transmission to the photosensors of ambient non-visible light.

16. The apparatus according to claim 1, wherein
the driving circuitry is configured to drive the electrodes to apply the currents in stimulation pulses of current, and
the driving circuitry is configured to regulate a number of the stimulation pulses in response to the modulation of the radiation emitted from the power source.

17. The apparatus according to claim 1, wherein
the driving circuitry is configured to drive the electrodes to apply the currents in stimulation pulses of current, and
the driving circuitry is configured to regulate a frequency of the stimulation pulses, in response to the modulation of the radiation emitted from the power source.

18. The apparatus according to claim 1, wherein
the driving circuitry is configured to drive the electrodes to apply the currents in stimulation pulses of current, and
the driving circuitry is configured to regulate a duration of each stimulation pulse, in response to the modulation of the radiation emitted from the power source.

19. The apparatus according to claim 1, wherein
the driving circuitry is configured to drive the electrodes to apply the currents in stimulation pulses of current, and
the driving circuitry is configured to regulate a pulse repetition interval of the stimulation pulses, in response to the modulation of the radiation emitted from the power source.

20. A method for modulating a parameter of an implant configured for implantation in a subject, the method comprising:
providing apparatus, comprising:
an external device, comprising:
a mount, configured to be placed in front of an eye of a subject; and
a power source coupled to the mount and configured to emit radiation that is outside of 380-750 nm; and
an intraocular device configured to be implanted entirely in the subject's eye, the intraocular device comprising:
an energy receiver, configured to receive the radiation from the power source and to generate a voltage drop in response thereto;
a plurality of stimulating electrodes;
a plurality of photosensors, each photosensor configured to detect photons and to generate a signal in response thereto; and
driving circuitry, coupled to the energy receiver and to the photosensors, and configured to receive the signals from the photosensors and to utilize the voltage drop to drive the electrodes to apply currents to a retina of the eye in response to the signals from the photosensors,
wherein the external device is configured to modulate the radiation emitted from the power source using an encoding protocol such that pulses of the radiation are encoded by the encoding protocol, and wherein the driving circuitry is configured to regulate a parameter of operation of the driving circuitry in response to the modulation of the radiation emitted from the power source, and wherein the driving circuitry is configured to control a sensitivity of the photosensors, by the regulating of the parameter by the driving circuitry,
emitting the radiation, from the power source to the intraocular device;
receiving an input from the subject, and in response to receiving the input from the subject, modulating the radiation emitted from the power source by using the encoding protocol such that the pulses of the radiation are encoded by the encoding protocol;
regulating the parameter of the driving circuitry of the intraocular device in response to the modulation of the radiation emitted from the power source; and
controlling the sensitivity of the photosensors, by the regulating of the parameter by the driving circuitry.

21. The method according to claim 20, wherein the method further comprises:
using the driving circuitry, driving currents into the electrodes of the intraocular device in stimulation pulses; and
in response to the modulation of the radiation, regulating at least one stimulation parameter selected from the group consisting of: a number of the stimulation pulses, a frequency of the stimulation pulses, a duration of each stimulation pulse, and a pulse repetition interval of the stimulation pulses.

* * * * *